United States Patent
Atalar et al.

(10) Patent No.: US 10,578,691 B2
(45) Date of Patent: Mar. 3, 2020

(54) GRADIENT MAGNETIC FIELD GENERATION MODULE USING PLURALITY OF COILS SO AS TO GENERATE GRADIENT MAGNETIC FIELD

(71) Applicant: Bilkent University, Ankara (TR)

(72) Inventors: Ergin Atalar, Ankara (TR); Soheil Taraghinia, Ankara (TR); Niyazi Koray Ertan, Ankara (TR)

(73) Assignee: Bilkent University, Ankara (TR)

( * ) Notice: Subject to any disclaimer, the term of this patent is extended or adjusted under 35 U.S.C. 154(b) by 0 days.

(21) Appl. No.: 15/813,445

(22) Filed: Nov. 15, 2017

(65) Prior Publication Data

US 2018/0120393 A1    May 3, 2018

Related U.S. Application Data

(63) Continuation of application No. PCT/KR2016/005160, filed on May 16, 2016.

(Continued)

(51) Int. Cl.
*G01R 33/385* (2006.01)
*A61B 5/055* (2006.01)
(Continued)

(52) U.S. Cl.
CPC .......... *G01R 33/3852* (2013.01); *A61B 5/055* (2013.01); *G01R 33/0023* (2013.01); *G01R 33/44* (2013.01)

(58) Field of Classification Search
CPC .............. G01R 33/0023; G01R 33/022; G01R 33/385; G01R 33/3852; G01R 33/04; A61B 5/055
See application file for complete search history.

(56) References Cited

U.S. PATENT DOCUMENTS

| 5,278,504 A | 1/1994 | Patrick |
| 5,382,904 A | 1/1995 | Pissanetsky |

(Continued)

FOREIGN PATENT DOCUMENTS

| JP | 2007167143 A | 7/2007 |
| JP | 2008168132 A | 7/2008 |

(Continued)

OTHER PUBLICATIONS

International Search Report dated Aug. 19, 2016 in corresponding PCT Patent Application Serial No. PCT/KR2016/005160.

(Continued)

*Primary Examiner* — Rishi R Patel
(74) *Attorney, Agent, or Firm* — Nelson Mullins Riley & Scarborough LLP; Thomas J. Engellenner; Reza Mollaaghababa (57) ABSTRACT

Provided is a gradient magnetic field generation module using multiple coils to generate a gradient magnetic field. Provided is a gradient magnetic field generation module including: a gradient coil formed inside a main magnet and generating a gradient magnetic field and including a plurality of coils; and a gradient amplifier controlling at least one of a shape of the gradient magnetic field, a strength of the gradient magnetic field, and slew rate of the gradient magnetic field generated by the gradient coil, in which the plurality of coils is grouped into a plurality of coil groups and current which flows in the plurality of coils is independently controlled by the unit of a group by the gradient amplifier.

9 Claims, 7 Drawing Sheets

Related U.S. Application Data (60) Provisional application No. 62/164,896, filed on May 21, 2015.

(51) Int. Cl.
*G01R 33/00* (2006.01)
*G01R 33/44* (2006.01)

(56) References Cited

U.S. PATENT DOCUMENTS

| | | | |
|---|---|---|---|
| 5,659,281 A | 8/1997 | Pissanetsky | |
| 6,016,439 A | 1/2000 | Acker | |
| 6,448,773 B1 | 9/2002 | Zhang | |
| 6,472,872 B1 | 10/2002 | Jack, Jr. | |
| 6,501,977 B1 * | 12/2002 | Kimmlingen | A61B 5/055 324/307 |
| 6,563,315 B1 * | 5/2003 | Boskamp | G01R 33/385 324/309 |
| 6,900,638 B1 * | 5/2005 | Yair | G01R 33/3852 324/309 |
| 7,202,734 B1 | 4/2007 | Raab | |
| 7,800,368 B2 | 9/2010 | Vaughan | |
| 8,125,225 B2 | 2/2012 | Koretsky | |
| 9,755,576 B2 | 9/2017 | Perreault | |
| 9,923,518 B2 | 3/2018 | Perreault | |
| 10,120,050 B2 | 11/2018 | Felweier | |
| 2001/0024122 A1 * | 9/2001 | Mulder | G01R 33/385 324/318 |
| 2007/0216409 A1 * | 9/2007 | Overweg | G01R 33/34046 324/262 |
| 2007/0279058 A1 | 12/2007 | Bulkes | |
| 2008/0272784 A1 * | 11/2008 | Harvey | G01R 33/385 324/318 |
| 2011/0254551 A1 | 10/2011 | Leussler | |
| 2014/0320132 A1 | 10/2014 | Schmale | |
| 2016/0181986 A1 | 6/2016 | Perreault | |
| 2016/0181987 A1 | 6/2016 | Perreault | |
| 2018/0011156 A1 | 1/2018 | Atalar | |
| 2018/0081003 A1 | 3/2018 | Atalar | |
| 2018/0292502 A1 | 10/2018 | Atalar | |

FOREIGN PATENT DOCUMENTS

| | | |
|---|---|---|
| JP | 2008-264101 A | 11/2008 |
| JP | 2013-000591 A | 1/2013 |
| JP | 2014083445 A | 5/2014 |
| KR | 10-0900862 B1 | 6/2009 |
| KR | 10-1503494 B1 | 3/2015 |

OTHER PUBLICATIONS

Gudino et al., "1.5T On-Coil Current-Mode Class-D (CMCD) Amplifier with Amplitude Modulation Feedback and Voltage-Mode Class-D (VMCD) Preamplifier," Proc. Intl. Soc. Mag. Reson. Med. 18 (2010).

International Search Report dated Aug. 22, 2016 in corresponding PCT Patent Application Serial No. PCT/KR2016/005150.

International Written Opinion dated Aug. 19, 2016 from PCT/KR2016/005160 (6 pages).

International Written Opinion dated Aug. 22, 2016 from PCT/KR2016/005150 (7 pages).

* cited by examiner

GRADIENT MAGNETIC FIELD GENERATION MODULE USING PLURALITY OF COILS SO AS TO GENERATE GRADIENT MAGNETIC FIELD

CROSS REFERENCE TO RELATED APPLICATIONS

This application is a continuation of International Patent Application No. PCT/KR2016/005160, filed on May 16, 2016, which claims the benefit of U.S. Provisional Patent Application Ser. No. 62/164,896, filed on May 21, 2015, each of which is hereby incorporated by reference in its entirety herein.

TECHNICAL FIELD

The present disclosure relates to a gradient magnetic field generation module, and particularly, to a module for generating various gradient magnetic fields.

BACKGROUND ART

Magnetic resonance imaging (MRI) provides information obtained through resonance after exposing an atomic nucleus to a magnetic field as an image. The resonance of the atomic nucleus refers to a phenomenon in which when a specific high frequency is incident in the atomic nucleus magnetized by an external magnetic field, the atomic nucleus in a low energy state is excited to a high energy state by absorbing high frequency energy. The atomic nuclei have different resonance frequencies depending on a type and the resonance is influenced by an intensity of an external magnetic field. There are innumerable atomic nuclei inside a human body and hydrogen atomic nuclei are generally used for photographing a magnetic resonance image.

A magnetic resonance imaging system may generate a gradient magnetic field in a magnetic resonance imaging apparatus. The generated gradient magnetic field may be used to create a section of a region to be photographed. In a method for generating the gradient magnetic field in the related art, a uniform gradient magnetic field cannot be generated, and as a result, there is inconvenience.

Accordingly, a method for generating various gradient magnetic fields in the magnetic resonance imaging system is being studied.

A prior art document related to the method is Patent Registration No. KR 10-1503494.

SUMMARY

The present disclosure discloses methods and systems for efficiently generating various gradient magnetic fields.

As a technical means for achieving the technical object, a first aspect of the present disclosure may provide a gradient magnetic field generation module including: a gradient coil formed inside a main magnet and generating a gradient magnetic field and including a plurality of coils; and a gradient amplifier controlling at least one of a shape of the gradient magnetic field, a strength of the gradient magnetic field, and a slew rate of the gradient magnetic field generated by the gradient coil, in which the plurality of coils is grouped into a plurality of coil groups and current which flows in the plurality of coils is independently controlled by the unit of a group and by the gradient amplifier.

The present disclosure can provide a method for generating various gradient magnetic fields.

BRIEF DESCRIPTION OF DRAWINGS

Various aspects are now described with reference to the drawings and like reference numerals are generally used to designate like elements. In the following embodiments, for a description purpose, multiple specific detailed matters are presented to provide general understanding of one or more aspects. However, it will be apparent that the aspect(s) can be executed without the detailed matters. In other examples, known structures and apparatuses are illustrated in a block diagram form in order to facilitate description of the one or more aspects.

DETAILED DESCRIPTION

Various embodiments will now be described with reference to drawings and like reference numerals are used to refer to like elements throughout all drawings. In the present specification, various descriptions are presented to provide appreciation of the present disclosure. However, it is apparent that the embodiments can be executed without the specific description. In other examples, known structures and apparatuses are presented in a block diagram form in order to facilitate description of the embodiments.

Terms used in the present specification will be described in brief and the present disclosure will be described in detail. Terms used in the present disclosure adopt general terms which are currently widely used as possible by considering functions in the present disclosure, but the terms may be changed depending on an intention of those skilled in the art, a precedent, emergence of new technology, etc. Further, in a specific case, a term which an applicant arbitrarily selects is present and in this case, a meaning of the term will be disclosed in detail in a corresponding description part of the invention. Accordingly, a term used in the present disclosure should be defined based on not just a name of the term but a meaning of the term and contents throughout the present disclosure.

Further, throughout the specification, unless explicitly described to the contrary, the word "comprise" and variations such as "comprises" or "comprising", will be understood to imply the inclusion of stated elements but not the exclusion of any other elements.

Further, the term "unit" or "module" used in the specification means software and hardware components and the "unit" or "module" performs predetermined roles. However, the "unit" or "module" is not a meaning limited to software or hardware. The "unit" or "module" may be configured to reside on an addressable storage medium and may be configured to play back one or more processors.

Accordingly, as one example, the "unit" or "module" includes components such as software components, object oriented software components, class components, and task components, processes, functions, attributes, procedures, subroutines, segments of a program code, drivers, firmware, microcode, circuitry, data, databases, data structures, tables, arrays, and variables. Functions provided in the components and the "units" or "modules" may be combined into a smaller number of components and "units" or "modules" or further separated into additional components and "units" or "modules".

An embodiment of the present disclosure will be described more fully hereinafter with reference to the accompanying drawings so as to be easily implemented by those skilled in the art. In addition, a part which is not related with the description is omitted in the drawings in order to clearly describe the present disclosure.

In the present specification, "image" may mean multi-dimensional data constituted by discrete image elements (e.g., pixels in a 2D image and voxels in a 3D image). For example, the image may include a medical image of an object, which are acquired by X-ray, CT, MRI, ultrasonic waves, and other medical imaging systems, and the like. Further, in the present specification, the "object" may include a person or an animal, or a part of the person or the animal. For example, the object may include organs including liver, heart, uterus, brain, breast, abdomen, and the like or a blood vessel. Further, the "object" may include a phantom. The phantom means a material that has a density of a living thing and a volume that is very proximate to an effective atomic number and can include a spherical phantom that has a similar property to a human body.

Further, in the present specification, a "user" as a medical specialist may be a doctor, a nurse, a medical technologist, a medical imaging expert, or the like and be a technician repairing a medical apparatus, but is not limited thereto.

Further, in the present specification, the term "magnetic resonance imaging (Mill)" means an image for an object obtained using a nuclear magnetic resonance principle.

In addition, in the present specification, the term "pulse sequence" means a series of signals repeatedly applied in the MRI apparatus. The pulse sequence may include a time parameter of an RF pulse, for example, a repetition time (TR) and a time to echo (TE).

Further, in the present specification, the term "TR" may mean the repetition time of the RF pulse. For example, the TR may mean a time between a transmission time of a first RF pulse and a transmission time of a second RF pulse.

Further, in the present specification, the term "pulse sequence schematic diagram" denotes an order in which the signals are applied in the MRI apparatus. For example, the pulse sequence schematic diagram may be a schematic diagram illustrating the RF pulse, a gradient magnetic field, a magnetic resonance signal, etc., with time.

Further, in the present specification, the term "spatial encoding" refers to obtaining spatial information along an axis (direction) of the gradient magnetic field by applying a linear gradient magnetic field that causes additional dephasing of a proton spindle in addition to dephasing of the proton spindle by an RF signal.

The MRI apparatus is an apparatus for acquiring an image of a single-layer portion of the object by expressing the intensity of a magnetic resonance (MR) signal for a radio frequency (RF) signal generated in a magnetic field of a specific intensity in contrast. For example, when the object is laid in a strong magnetic field and thereafter, the RF signal to resonate only a specific atomic nucleus (e.g., a hydrogen atomic nucleus, etc.) is irradiated to the object and stopped, the magnetic resonance signal is emitted from the specific atomic nucleus and the MRI apparatus may obtain an MR image by receiving the magnetic resonance signal. The magnetic resonance signal refers to the RF signal irradiated from the object. The magnitude of the magnetic resonance signal may be determined by the concentration of predetermined atoms (e.g., hydrogen, etc.) contained in the object, a relaxation time T1, a relaxation time T2, and a flow of a bloodstream.

The MRI apparatus includes features different from other imaging apparatuses. Unlike imaging apparatuses, such as CT, where acquisition of an image is dependent on a direction of detecting hardware, the MRI apparatus may acquire a two-dimensional image or a three-dimensional volume image directed to any point. Further, unlike CT, X-ray, PET, and SPECT, the MRI apparatus does not expose the object and an examinee to radiation, and may acquire an image having a high soft tissue contrast. Therefore, a neurological image, an intravascular image, a musculoskeletal image, and an oncologic image in which it is important to clearly describe abnormal tissue may be obtained.

A three-dimensional volume of the object may include a three-dimensional shape of a person or animal, or a part of the person or the animal. For example, the volume of the object may include the three-dimensional shape of organs including liver, heart, uterus, brain, breast, abdomen, and the like or a blood vessel, etc.

When the MRI apparatus intends to acquire information of the 3D volume of the object in a short time, it is possible to acquire a plurality of sheets of slice images in the direction of the slices constituting the 3D volume. When images of a plurality of slices are photographed, it is common to sequentially photograph the slice images as many as the slices, but taking the slice images sequentially may require a lot of photographing time.

In a multi-slice scheme, when each slice image is acquired in a plurality of repetition time (TR) intervals, data for each slice is acquired in each TR interval in a cross direction to shorten a photographing time. For example, there is a dead time when the TR interval is much longer than an active time required for cross-section selection, phase encoding, and frequency encoding. In the multi-slice scheme, in order to obtain information on another cross section after obtaining information on one cross section in each TR interval, the dead time may be used.

In a simultaneous multi-slice (SMS) scheme, the plurality of slices is simultaneously excited to reduce a scan time to simultaneously acquire the magnetic resonance signals from the plurality of slices through a plurality of coils and a difference in coil sensitivity information which exists between the slices is used to separate the magnetic resonance signals for each slice. The coil sensitivity information may mean a sensitivity to receive different magnetic resonance signals depending on a location of each coil among the plurality of coils.

The simultaneous multi-slice scheme may correspond to parallel imaging, and the parallel imaging may include a sense scheme or a GRAPPA scheme.

Figure 1:
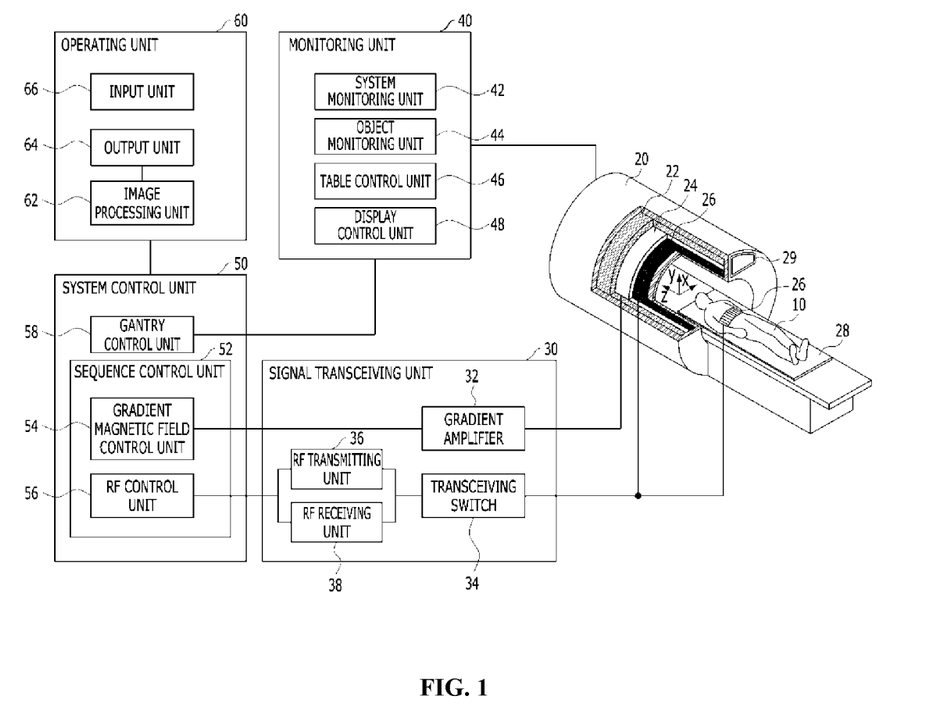
FIG. 1 is a block diagram illustrating a magnetic resonance imaging apparatus according to an embodiment of the present disclosure.

FIG. 1 is a block diagram illustrating a magnetic resonance imaging apparatus according to an embodiment of the present disclosure.

Referring to FIG. 1, a magnetic resonance imaging apparatus may include a gantry 20, a signal transceiving unit 30, a monitoring unit 40, a device control unit 50, and an operating unit 60.

The gantry 20 may block electromagnetic waves generated by a main magnet 22, a gradient coil 24, an RF coil 26, etc. from being radiated to the outside. The gantry 20 may include a bore therein. An electromagnetic field and a gradient magnetic field may be formed in the bore and an RF signal may be irradiated from the bore toward an object 10.

The main magnet 22, the gradient coil 24, and the RF coil 26 may be disposed in a predetermined direction of the gantry 20. The predetermined direction may include a coaxial cylindrical direction, etc. The object 10 may be positioned on a table 28 insertable into a cylinder along a horizontal axis of the cylinder.

The main magnet 22 may generate a static magnetic field for aligning a magnetic dipole moment of the atomic nuclei included in the object 10 in a predetermined direction.

As the magnetic field generated by the main magnet is stronger and more uniform, a relatively precise and accurate MR image with respect to the object 10 may be obtained.

According to the embodiment of the present disclosure, a magnetic resonance circuit system may include a gradient magnetic field generation module. The gradient magnetic field generation module means a module which generates the gradient magnetic field to form a gradient magnetic field. The gradient magnetic field generation module may include a gradient amplifier 32 and a gradient magnetic field coil 24.

The gradient amplifier 32 can apply the current to the gradient magnetic field coil 24 under the control of a gradient magnetic field control unit 54. In this case, the gradient amplifier 32 may supply the current to the gradient magnetic field coil 24 for a predetermined time and stop supplying the current when the predetermined time has elapsed.

According to the embodiment of the present disclosure, the gradient amplifier 32 applies various currents to the coil group under the control of the gradient magnetic field control unit 54 to generate gradient magnetic fields having various magnitudes and directions. For example, the gradient amplifier 32 applies the current to the coil group to control at least one of a shape of the gradient magnetic field, the strength of the gradient magnetic field, and a slew rate of the gradient magnetic field generated by the coil group.

The gradient coil 24 may include X, Y, and Z coils that generate a gradient magnetic field in mutually orthogonal X-, Y-, and Z-axis directions. The gradient coil 24 may provide positional information of each part of the object 10 by inducing resonance frequencies differently for each part of the object 10.

The RF coil 26 may irradiate RF signals to a patient and receive magnetic resonance signals emitted from the patient. For example, the RF coil 26 may transmit an RF signal having a frequency equal to a frequency of a processional motion toward the atomic nucleus which performs the processional motion and thereafter, stop transmission of the RF signal and receive the magnetic resonance signal emitted from the patient.

For example, the RF coil 26 may generate an electromagnetic signal, having a radio frequency corresponding to the type of atomic nucleus, for example, an RF signal, and apply the generated RF signal to the object 10 so as to transition a certain atomic nucleus from a low energy state to a high energy state. When the electromagnetic signal generated by the RF coil 26 is applied to the certain atomic nucleus, the certain atomic nucleus may transition from the low energy state to the high energy state. Thereafter, when the electromagnetic wave generated by the RF coil 26 is removed, the atomic nucleus to which the electromagnetic wave has been applied may emit electromagnetic waves having a Larmor frequency while transiting from the high energy state to the low energy state. In other words, when the application of the electromagnetic signal to the atomic nucleus is interrupted, while an energy level from high energy to low energy is changed in the atomic nucleus to which the electromagnetic wave is applied is changed, the electromagnetic wave having the Larmor frequency may be emitted. Here, the Larmor frequency may mean a frequency at which magnetic resonance is induced in the atomic nucleus.

The RF coil 26 may receive the electromagnetic signals irradiated from the atomic nuclei inside the object 10. The RF coil 26 may be implemented as one RF transceiving coil having both a function of generating the electromagnetic wave having the radio frequency corresponding to the type of atomic nucleus and a function of receiving the electromagnetic waves irradiated from the atomic nucleus.

Further, the RF coil 26 may be implemented as each of a transmission RF coil having the function of generating the electromagnetic wave having the radio frequency corresponding to the type of atomic nucleus and a reception RF coil having the function of receiving the electromagnetic wave irradiated from the atomic nucleus.

Further, the RF coil 26 may be fixed to the gantry 20 and may be removable. The removable RF coil 26 may include RF coils for a portion of the object including a head RF coil, a thorax RF coil, a leg RF coil, a neck RF coil, a shoulder RF coil, a wrist RF coil, and an ankle RF coil.

Further, the RF coil 26 may communicate with an external device by a wired and/or wireless manner and may perform even dual tune communication according to a communication frequency band.

In addition, the RF coil 26 may include a birdcage coil, a surface coil, and a transverse electromagnetic coil (TEM coil) according to a structure of the coil.

In addition, the RF coil 26 may include a transmission-only coil, a reception-only coil, and a transmission/reception-combination coil according to a method of transceiving the RF signal.

Further, the RF coil 26 may include RF coils of various channels such as 16 channels, 32 channels, 72 channels, and 144 channels.

The gantry 20 may further include a display 29 positioned outside the gantry 20 and a display (not illustrated) positioned inside the gantry 20. Predetermined information may be provided to the user or the object via the displays positioned inside and outside of the gantry 20.

The signal transceiving unit 30 may control a gradient magnetic field formed in the gantry 20 according to a predetermined MR sequence and control transmission and reception of the RF signal and the magnetic resonance signal.

The signal transceiving unit 30 may include a gradient amplifier 32, a transceiving switch 34, an RF transmitting unit 36, and an RF receiving unit 38.

The gradient amplifier 32 may drive the gradient coil 24 included in the gantry 20 and supply a pulse signal for generating the gradient magnetic field to the gradient coil 24 under the control of the gradient magnetic field control unit 54.

The gradient magnetic field control unit 54 may control the pulse signal supplied from the gradient amplifier 32 to the gradient coil 24. By controlling the pulse signal supplied to the gradient coil 24, the gradient magnetic fields in X-axis, Y-axis, and Z-axis directions may be synthesized. The pulse signal may be implemented by current.

The RF transmitting unit 36 and the RF receiving unit 38 may drive the RF coil 26. The RF transmitting unit 36 may supply the RF pulse of the Larmor frequency to the RF coil 26 and the RF receiving unit 38 may receive the magnetic resonance signal received by the RF coil 26.

The transceiving switch 34 may adjust transmission/reception directions of the RF signal and the magnetic resonance signal. For example, the transceiving switch 34 may cause the RF signal to be irradiated to the object 10 through the RF coil 26 during a transmission mode and the magnetic resonance signal from the object 10 through the RF coil 26 to be received during a reception mode. The transceiving switch 34 may be controlled by a control signal from an RF control unit 56.

The monitoring unit 40 may monitor or control the gantry 20 or devices mounted on the gantry 20. The monitoring unit 40 may include a system monitoring unit 42, an object monitoring unit 44, a table control unit 46, and a display control unit 48.

The system monitoring unit 42 may monitor and control a state of the static magnetic field, the state of the gradient magnetic field, the state of the RF signal, the state of the RF coil, the state of a table, the state of a device for measuring body information of the object, a power supply state, the state of a heat exchanger, the state of a compressor, and the like.

The object monitoring unit 44 may monitor the state of the object 10. For example, the object monitoring unit 44 may include a camera for observing a motion or a position of the object 10, a respiration measurer unit for measuring respiration of the object 10, an ECG measurer for measuring an electrocardiogram of the object 10, or a body temperature measurer for measuring a body temperature of the object 10.

The table control unit 46 may control movement of the table 28 at which the object 10 is positioned. The table control unit 46 may control the movement of the table 28 according to sequence control of the sequence control unit 50. For example, in moving imaging of the object, the table control unit 46 may continuously or intermittently move the table 28 according to the sequence control by the sequence control unit 50 to thereby photograph the object in a field of view (FOV) larger than the FOV of the gantry.

The display control unit 48 may control the displays positioned outside and inside the gantry 20. For example, the display control unit 48 may control on/off of the displays positioned outside and inside the gantry 20 or a screen to be output to the display, etc. Further, when a speaker is positioned inside or outside the gantry 20, the display control unit 48 may control the on/off of the speaker or a sound to be output through the speaker, etc.

The system control unit 50 may include a sequence control unit 52 for controlling a sequence of signals formed in the gantry 20 and a gantry control unit 58 for controlling the devices mounted on the gantry 20.

The sequence control unit 52 may include the gradient magnetic field control unit 54 for controlling the gradient amplifier 32 and the RF control unit 56. The RF control unit 56 may control the RF transmitting unit 36, the RF receiving unit 38, and the transceiving switch 34.

The sequence control unit 52 may control the gradient amplifier 32, the RF transmitting unit 36, the RF receiving unit 38, and the transceiving switch 34 according to a pulse sequence received from the operating unit 60.

Here, the pulse sequence may include all information required for controlling the gradient amplifier 32, the RF transmitting unit 36, the RF receiving unit 38, and the transceiving switch 34 and may include, for example, information on the intensity, an application time, an application timing, and the like of the pulse signal applied to the gradient coil 24.

The operating unit 60 may instruct the pulse sequence information to the system control unit 50 and control an operation of the entire MRI apparatus.

The operating unit 60 may include an image processing unit 62 for processing the magnetic resonance signal received from the RF receiving unit 38, an output unit 64, and an input unit 66.

The image processing unit 62 processes the magnetic resonance signal received from the RF receiving unit 38 to generate magnetic resonance image data for the object 10.

The image processing unit 62 may perform various signal processing such as amplification, frequency conversion, phase detection, low frequency amplification, filtering, and the like on the magnetic resonance signal received by the RF receiving unit 38.

The image processing unit 62, for example, arranges digital data in k-space data (also referred to as, for example, a Fourier space or a frequency space) of a memory and performs two-dimensional or three-dimensional Fourier transformation of the data to reconfigure the data into image data.

Further, the image processing unit 62 may perform synthesis processing or difference arithmetic processing of the image data as necessary.

The synthesis processing may include addition processing for a pixel, maximum value projection (MW) processing, and the like. Further, the image processing unit 62 may store not only the reconfigured image data but also the image data subjected to the synthesis processing or the difference arithmetic processing in a memory (not illustrated) or an external server.

In addition, various signal processing applied to the magnetic resonance signal by the image processing unit 62 may be performed in parallel. For example, a plurality of magnetic resonance signals may be reconfigured into the image data by applying signal processing in parallel to the plurality of magnetic resonance signals received by a multi-channel RF coil.

The output unit 64 may output the image data or the reconfigured image data generated by the image processing unit 62 to the user. In addition, the output unit 64 may output information required for the user to operate the MRI apparatus, such as a UI (user interface), user information, or object information.

The output unit 64 may include the speaker, a printer, a CRT display, an LCD display, a PDP display, an OLED display, an FED display, an LED display, a VFD display, a DLP display, a PFD display, a 3D display, a transparent display, and the like and may include a variety of output devices within other scopes which are apparent to those skilled in the art.

The user may input object information, parameter information, a scan condition, the pulse sequence, information on image synthesis and calculation of difference, and the like using the input unit 66. The input unit 66 may include a keyboard, a mouse, a trackball, a voice recognition unit, a gesture recognition unit, a touch screen, and the like and may include various input devices within the other scopes which are apparent to those skilled in the art.

FIG. 1 illustrates the signal transceiving unit 30, the monitoring unit 40, the system control unit 50, and the operating unit 60 as separate objects, but those skilled in the art will be able to sufficiently appreciate that functions performed by the signal transceiving unit 30, the monitoring unit 40, the system control unit 50, and the operating unit 60, respectively may be performed in different objects. For example, it is described above that the image processing unit 62 converts the magnetic resonance signal received by the RF receiving unit 38 into a digital signal, but the conversion into the digital signal may be autonomously performed by the RF receiving unit 38 or the RF coil 26.

The gantry 20, the RF coil 26, the signal transceiving unit 30, the monitoring unit 40, the system control unit 50, and the operating unit 60 may be connected to each other wirelessly or by wire and may further include a device (not illustrated) for synchronizing clocks with each other when the gantry 20, the RF coil 26, the signal transceiving unit 30, the monitoring unit 40, the system control unit 50, and the operating unit 60 are connected to each other wirelessly.

As communication among the gantry 20, the RF coil 26, the signal transceiving unit 30, the monitoring unit 40, the system control unit 50, and the operating unit 60, a high-speed digital interface such as low voltage differential signaling (LVDS), or the like, asynchronous serial communication such as universal asynchronous receiver transmitter (UART), false synchronization serial communication, a low-latency type network protocol such as a controller area network (CAN), or the like, an optical communication, or the like may be used and various communication methods may be used in the scope which is apparent to those skilled in the art.

Figure 2A:
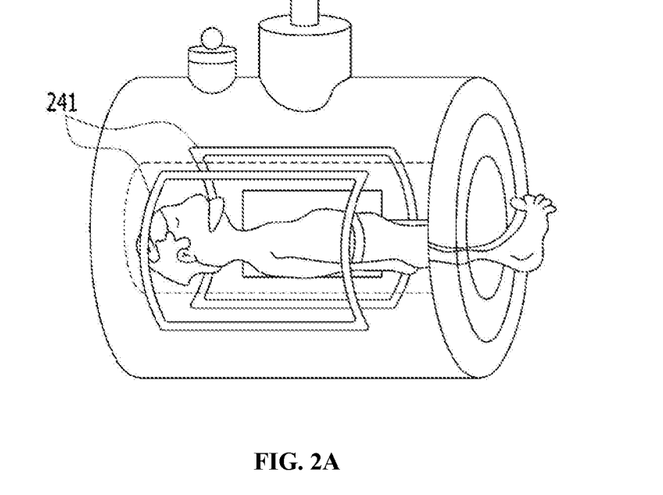
FIGS. 2A, 2B, and 2C illustrate a structure of a gradient coil according to an embodiment of the present disclosure.
Figure 2B:
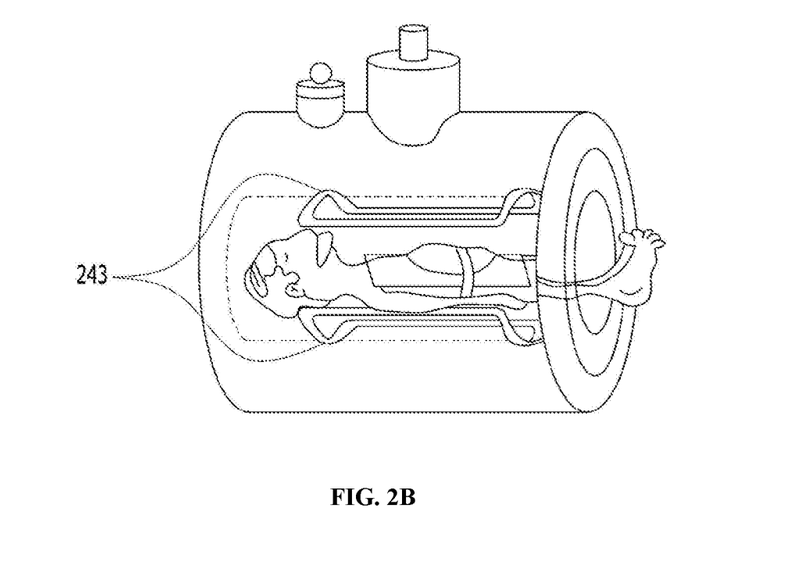
Figure 2C:
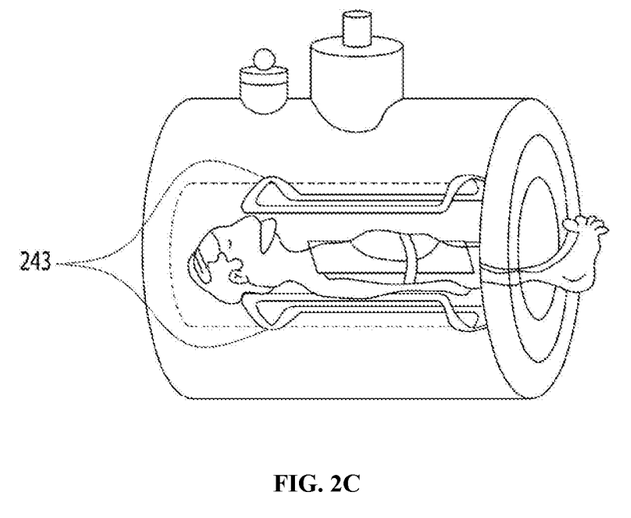

FIGS. 2A, 2B, and 2C illustrate a structure of a gradient coil according to an embodiment of the present disclosure.

According to an embodiment of the present disclosure, a magnetic resonance system 1000 may include a gradient magnetic field generation module. The gradient magnetic field generation module may be defined as a module for forming the gradient magnetic field by generating the gradient magnetic field. The gradient magnetic field generation module may include the gradient amplifier 32 and the gradient magnetic field coil 24.

According to an embodiment of the present disclosure, the gradient coil 24 changes the intensity of the main magnetic field by the main magnet 22 to make a temporary gradient magnetic field. The magnetic resonance imaging system 100 may acquire positional information of an atomic nucleus by using the generated gradient magnetic field.

The gradient coil 24 may include an X-axis gradient coil, a Y-axis gradient coil, and a Z-axis gradient coil, but is not limited thereto.

When current flows onto the Z-axis gradient coil 245 for a predetermined time, the strength of the magnetic field may further increase in a magnetic field direction having the same polarity as a magnetic field made by the Z-axis gradient coil 245. In addition, the strength of the magnetic field may be reduced by the Z-axis gradient coil 245 which makes an inverse polarity to the main magnetic field. As a result, the gradient magnetic field may be generated. In this case, a resonance frequency may be changed to be larger or smaller depending on the strength of the gradient magnetic field.

When the Z-axis gradient coil 245 generates resonance in a specific fragment selected as a Z axis, if the current is applied to the Y-axis gradient coil 243 of the specific fragment for a predetermined time, the resonance frequency may vary according to the position of a Y axis while the current flows. Further, when the current is removed, the resonance frequency may be changed to an original frequency again.

However, even though the resonance frequencies of the atomic nuclei experiencing magnetic fields having different strengths along the Y axis become constant again, the atomic nuclei rotate in a state where a magnitude of a rotation phase is changed according to the position of the Y axis. In other words, even though a rotation frequency of the atomic nucleus is constant, the atomic nucleus is changed in phase value according to the position, such as an atomic nucleus which rotates at a fast position, an atomic nucleus which rotates at a slow position, or the like. This is called phase encoding.

In the case where the current is applied to the X-axis gradient coil 241 for a moment when a signal is generated while in a cross section selected as the Z axis is phase-encoded, the rotation frequency may be changed along the X axis (for example, frequency encoding) and a signal combined with a plurality of frequencies may be generated according to the position of the atomic nucleus. The magnetic resonance imaging system may acquire the position of the X axis using the signal combined with the plurality of frequencies.

FIG. 2A is a diagram illustrating the X-axis gradient coil 241 according to an embodiment of the present disclosure. When the current flows in the X-axis gradient coil 241, the X-axis gradient coil 241 may generate the gradient magnetic field in the X-axis direction and the generated gradient magnetic field may change a phase and a frequency of the atomic nucleus or a combination thereof.

FIG. 2B is a diagram illustrating the Y-axis gradient coil 243 according to an embodiment of the present disclosure. When the current flows in the Y-axis gradient coil 243, the Y-axis gradient coil 243 may generate the gradient magnetic field in the Y-axis direction and the generated gradient magnetic field may change the phase and the frequency of the atomic nucleus or the combination thereof.

FIG. 2C is a diagram illustrating the Z-axis gradient coil 245 according to an embodiment of the present disclosure. When the current flows in the Z-axis gradient coil 245, the Z-axis gradient coil 245 may generate the gradient magnetic field in the Z-axis direction and the generated gradient magnetic field may change the phase and the frequency of the atomic nucleus or the combination thereof.

The Z-axis gradient coil 245 according to the embodiment of the present disclosure may include a plurality of coils. For example, the gradient coil 24 may include a plurality of coils having a loop shape. In this case, the plurality of coils may be grouped into a plurality of coil groups and the magnetic resonance imaging system may control the plurality of coils by the unit of the group.

Further, the plurality of coils may be grouped into a plurality of pair coil groups and the magnetic resonance imaging system may control the plurality of coils by the unit of the pair coil group.

Figure 3:
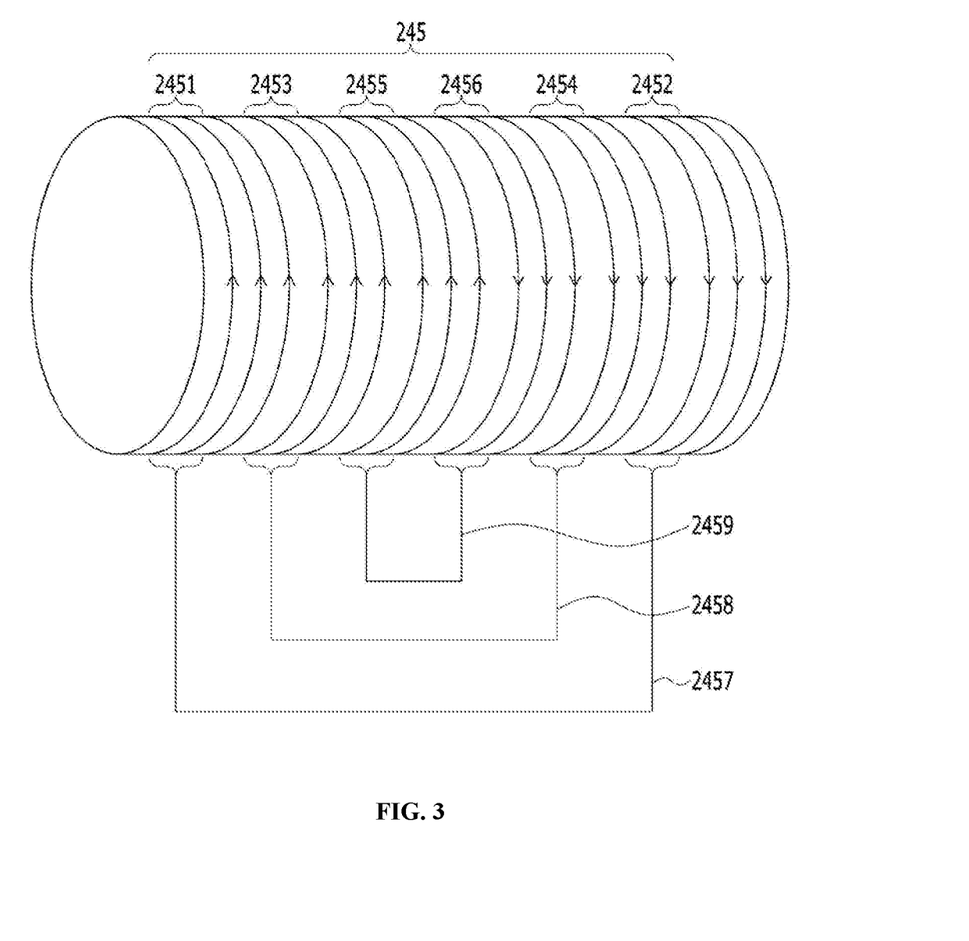
FIG. 3 is a diagram for describing a Z-axis gradient coil according to an embodiment of the present disclosure.

FIG. 3 is a diagram for describing a Z-axis gradient coil according to an embodiment of the present disclosure.

The Z-axis gradient coil 245 according to the embodiment of the present disclosure may receive the current from the gradient amplifier 32.

According to the embodiment of the present disclosure, the gradient amplifier 32 applies various currents to the Z-axis gradient coil 245 under the control of the gradient magnetic field control unit 54 to generate gradient magnetic fields having various strengths and directions. For example, the gradient amplifier 32 applies the current to the Z-axis gradient coil 245 to control at least one of a shape of the gradient magnetic field, the strength of the gradient magnetic field, and a slew rate of the gradient magnetic field generated by the coil group.

In this case, the gradient amplifier 32 may apply the current to the Z-axis gradient coil 245 by the unit of the coil group. For example, the gradient amplifier 32 may control at least one of the shape of the gradient magnetic field, the strength of the gradient magnetic field, and the slew rate of the gradient magnetic field by the unit of the coil group by applying the current to the coil group by the unit of the group.

The gradient amplifier 32 may control the gradient magnetic field coil 24 so as for the gradient magnetic field coil 24 to generate the gradient magnetic field under the control of the gradient magnetic field control unit 54. In this case, the gradient amplifier 32 may control the gradient magnetic field coil 24 according to a predetermined program.

The Z-axis gradient coil 245 according to the embodiment of the present disclosure may include a plurality of coils. For example, the gradient coil 24 may include a plurality of coils having a loop shape.

In this case, the plurality of coils may be grouped into a plurality of coil groups according to the positions of the coils. For example, two or more coils adjacent to each other may be grouped so that the plurality of coils may be grouped. One coil group may include one coil and may include the plurality of coils, but is not limited thereto.

The magnetic resonance imaging system may control the plurality of coils by the unit of the group. For example, current having the same magnitude may flow in the coils included in the coil group. Further, current in the same direction may flow on the coils included in the coil group. In addition, current which flows in the coils included in a first coil group and current which flows in the coils included in the second coil group may be different in at least one of the magnitude and the direction.

The plurality of coil groups may be grouped into a plurality of pair coil groups. The pair coil group may be configured by a group of coil groups in which the current of the same magnitude flows and the current flows in an opposite direction among the plurality of coil groups.

For example, the first coil group 2451 and the second coil group 2452 among the plurality of coil groups may be grouped into the pair coil group. In this case, the direction of the current flowing in the first coil group 2451 and the direction of the current flowing in the second coil group may be opposite directions. Further, the magnitude of the current flowing in the first coil group 2451 and the magnitude of the current flowing in the second coil group may be the same as each other.

The Z-axis gradient coil 245 may include a plurality of pair coil groups. For example, the Z-axis gradient coil 24 may include three pair coil groups, but is not limited thereto.

According to the embodiment of the present disclosure, the magnitude of the current flowing in the coils included in the Z-axis gradient coil 245 may be controlled by the unit of the pair coil group. For example, current having the same magnitude may flow on the coils included in the same pair coil group. Further, the magnitude of the current flowing in the coils included in the first pair coil group 2457 and the magnitude of the current flowing in the coils included in the second pair coil group 2458 may be different from each other.

According to the embodiment of the present disclosure, the coils included in the coil group may be arranged at uniform intervals. For example, an interval between a first coil and a second coil included in the first coil group 2451 may be the same as the interval between the second coil and a third coil included in the first coil group 2451.

According to another embodiment of the present disclosure, the coils included in the pair coil group may be arranged at uniform intervals. For example, the interval between the first coil and the second coil of the first coil group 2451 included in the first pair coil group 2457 may be the same as the interval between the third coil and a fourth coil of the second coil group 2452 included in the first pair coil group 2457.

According to another embodiment of the present disclosure, all of the coils included in the coil group may be arranged at uniform intervals. For example, the intervals between the coils included in the plurality of coil groups may all be the same. For example, the interval between the coils included in the first coil group 2451, the interval between the coils included in the second coil group 2452, the interval between the coils included in a third coil group 2453, the interval between the coils included in a fourth coil group 2454, the interval between the coils included in the fifth coil group 2455, and the interval between the coils included in the sixth coil group 2456 may be all the same.

In this case, the interval between adjacent coil groups may be different from the interval between the coils. For example, the interval between the third coil group 2453 adjacent to the first coil group 2451 and the first coil group 2451 may be different from the interval between the coils included in the first coil group 2451.

According to the embodiment of the present disclosure, the coil groups included in the pair coil group may be arranged according to the positions of other coil groups included in the pair coil group.

For example, another coil group included in the same pair coil group as the first coil group on a left side may be located first on a right side among the coil groups. Further, another coil group included in the same pair coil group as the second coil group on the left side may be located second on the right side among the coil groups. In addition, another coil group included in the same pair coil group as the third coil group on the left side may be located third on the right side among the coil groups.

According to the embodiment of the present disclosure, the magnetic resonance imaging system 100 may generate various gradient magnetic fields by controlling the coils included in the Z-axis gradient coil 245 by the unit of the group. For example, the magnetic resonance imaging system 100 may generate a linear gradient magnetic field and generate a non-linear gradient magnetic field by controlling the coils included in the Z-axis gradient coil 245 by the unit of the group, but is not limited thereto.

Further, the magnetic resonance imaging system 100 may variously change the strength of the gradient magnetic field formed at a bore by controlling the coils included in the Z-axis gradient coil 245 by the unit of the group. For example, the magnetic resonance imaging system 100 may generate a gradient magnetic field having the larger strength in a specific part than the gradient magnetic fields in other parts by controlling the coils included in the gradient coil 24 by the unit of the group.

The magnetic resonance imaging system 100 may variously control the intensity and the strength of the gradient magnetic field formed at the bore by variously controlling the coils included in the Z-axis gradient coil 245 by the unit of the group.

According to the embodiment of the present disclosure, the Z-axis gradient magnetic field coil 245 may generate at least one of an X-axis gradient magnetic field, a Y-axis gradient magnetic field, and a Z-axis gradient magnetic field. For example, the gradient amplifier 32 may generate at least one of the X-axis gradient magnetic field, the Y-axis gradient magnetic field, and the Z-axis gradient magnetic field by applying various current to the Z-axis gradient magnetic field coil 245.

According to another embodiment of the present disclosure, a structure and a function of the Z-axis gradient magnetic field coil 245 may be applied to at least one of the X-axis gradient magnetic field coil 241 and the Y-axis gradient magnetic field coil 243. As a result, at least one of the X-axis gradient magnetic field coil 241 and the Y-axis gradient magnetic field coil 243 may generate various gradient magnetic fields.

Figure 4:
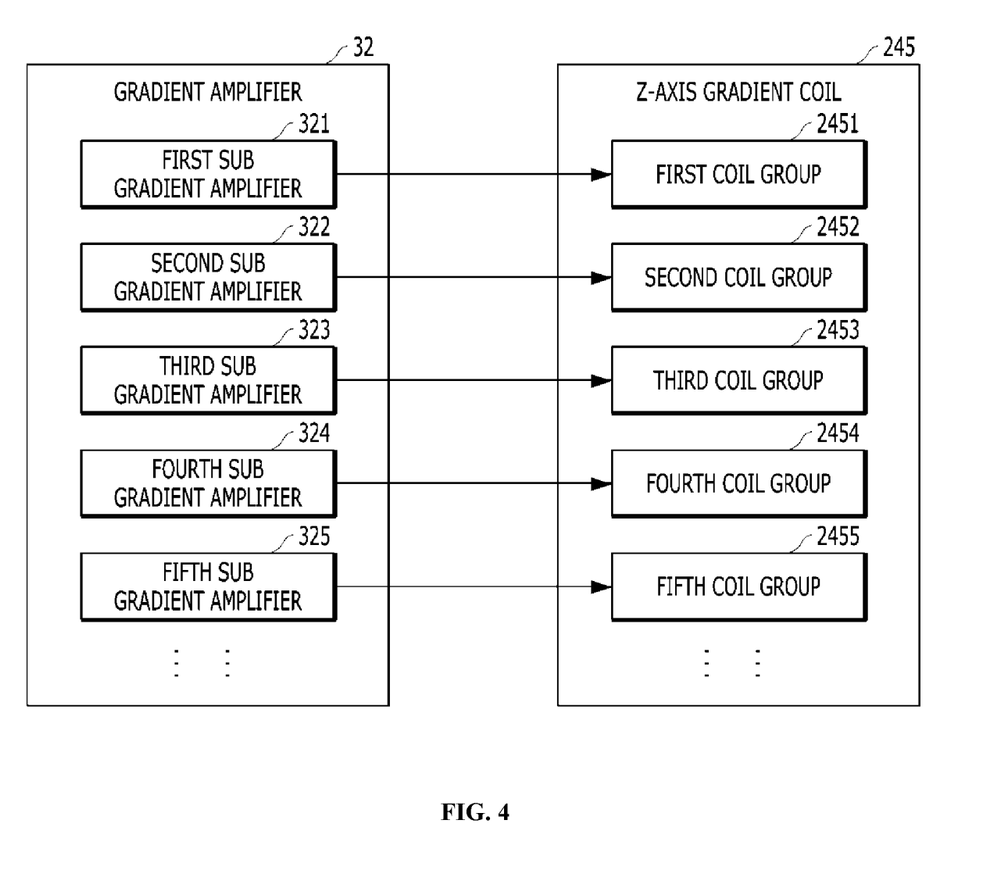
FIG. 4 is a diagram for describing an operation of a gradient amplifier according to an embodiment of the present disclosure.

FIG. 4 is a diagram for describing the gradient amplifier according to an embodiment of the present disclosure.

According to the embodiment of the present disclosure, the gradient amplifier 32 may include a plurality of sub gradient amplifiers. For example, the gradient amplifier 32 means a group of the sub gradient amplifier and the sub gradient amplifier may amplify the current to apply the amplified current to the gradient coil 24.

According to the embodiment of the present disclosure, the sub gradient amplifier may match the coil group included in the Z-axis gradient coil 245. For example, one sub gradient amplifier may match one coil group. In this case, the sub gradient amplifier may amplify the current and apply the amplified current to the coil group. The coil groups may be independently driven by a plurality of sub gradient amplifiers, respectively.

For example, a first sub gradient amplifier 321 may match the first coil group 2451. The first sub gradient amplifier 321 may apply current having the same magnitude and the same direction to at least one coil included in the first coil group 2451. Further, a second sub gradient amplifier 322 may match the second coil group 2452 and the second sub gradient amplifier 322 may apply current having the same magnitude and the same direction to at least one coil included in the second coil group 2452.

In this case, the magnitude of the current applied to the first coil group 2451 may be different from the magnitude of the current applied to the second coil group 2452. Further, the direction of the current applied to the first coil group 2451 may be different from the direction of the current applied to the second coil group 2452 and the magnitude and the direction of the current applied to the first coil group 2451 may be different from the magnitude and the direction of the current applied to the second coil group 2452 and the present disclosure is not limited thereto.

For example, the first sub gradient amplifier 321 may apply first-direction current to the first coil group 2451. Further, the second sub gradient amplifier 322 may apply second-direction current to the second coil group 2452. In this case, the first sub gradient amplifier 321 and the second sub gradient amplifier 322 apply currents having the same magnitude, respectively to generate the gradient magnetic field.

Figure 5:
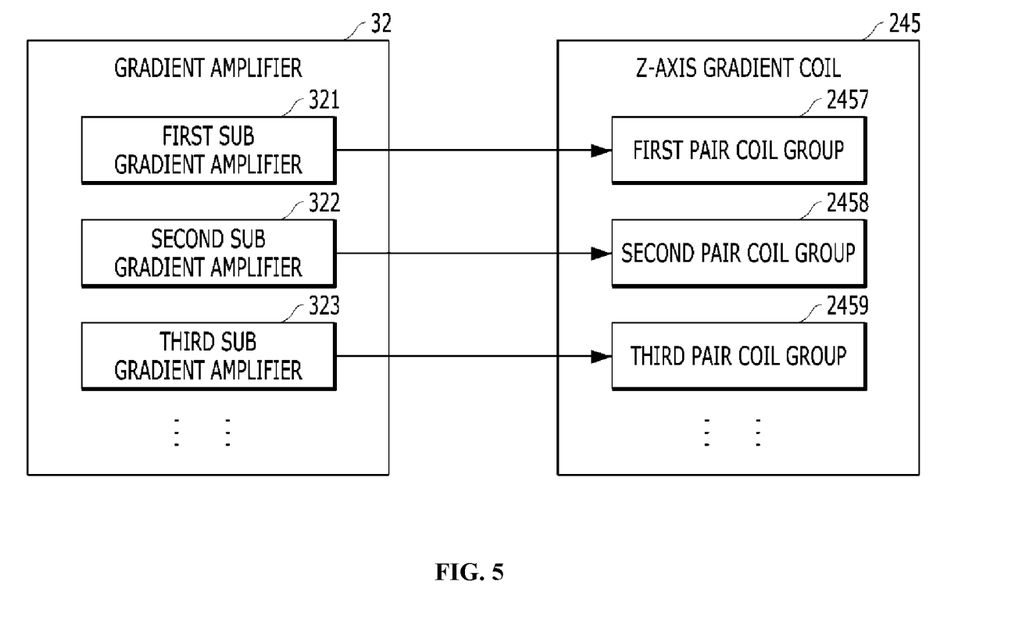
FIG. 5 is a diagram for describing an operation of a gradient amplifier according to another embodiment of the present disclosure.

FIG. 5 is a diagram for describing a gradient amplifier according to another embodiment of the present disclosure.

According to the embodiment of the present disclosure, the gradient amplifier 32 may include a plurality of sub gradient amplifiers. For example, the gradient amplifier 32 means a group of the sub gradient amplifiers and the sub gradient amplifiers may amplify the current to apply the amplified current to the gradient coil 24.

According to the embodiment of the present disclosure, the sub gradient amplifier may match the pair coil group included in the Z-axis gradient coil 245. For example, one sub gradient amplifier may match one pair coil group. In this case, the sub gradient amplifier may amplify the current and apply the amplified current to the pair coil group. The pair coil groups may be independently driven by a plurality of sub gradient amplifiers, respectively.

For example, the first sub gradient amplifier 321 may match the first pair coil group 2457. The first sub gradient amplifier 321 may apply current having the same magnitude to the plurality of coils included in the first pair coil group 2457. Further, the second sub gradient amplifier 322 may match the second pair coil group 2458 and the second sub gradient amplifier 322 may apply current having the same magnitude to the plurality of coils included in the second pair coil group 2458.

In this case, the magnitude of the current applied to the first pair coil group 2457 may be different from the magnitude of the current applied to the second pair coil group 2458.

According to the embodiment of the present disclosure, the first sub gradient amplifier 321 may apply first-direction current to the first coil group 2451 included in the first pair coil group 2457. Further, the first sub gradient amplifier 321 applies current in a direction opposite to a first direction to the second coil group 2452 included in the first pair coil group 2457 to generate the gradient magnetic field.

According to the embodiment of the present disclosure, the first sub gradient amplifier 321 applies current to both the first coil group 2451 and the second coil group 2452 to generate the gradient magnetic field.

Figure 6:
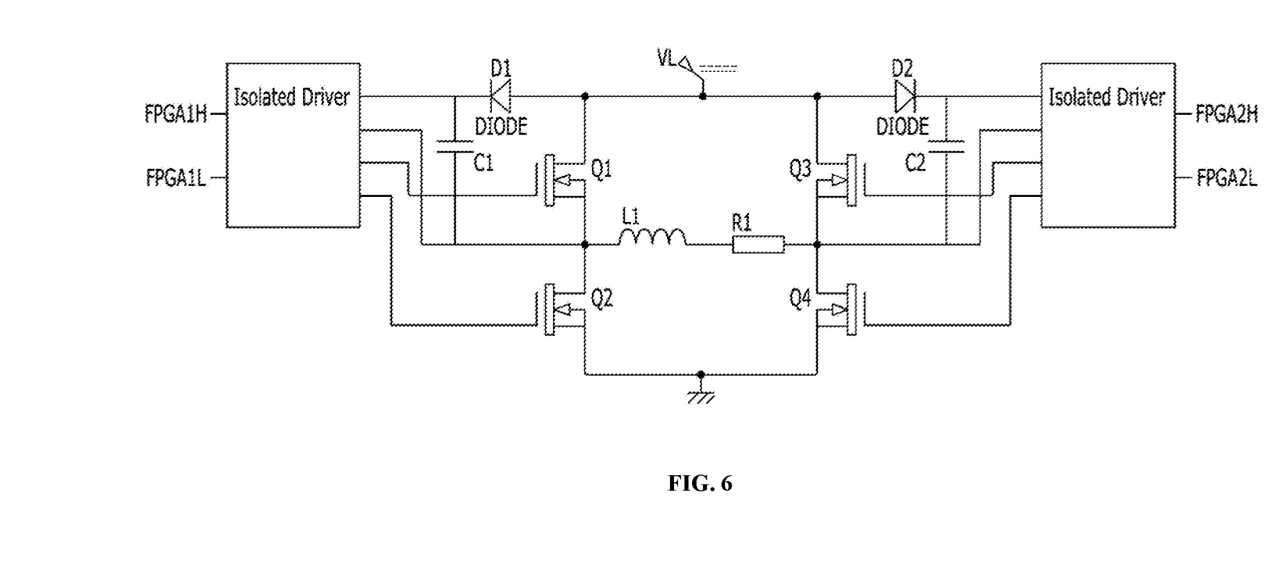
FIG. 6 is a circuit diagram for describing the gradient amplifier according to an embodiment of the present disclosure.

FIG. 6 is a circuit diagram for describing the gradient amplifier according to an embodiment of the present disclosure.

According to the embodiment of the present disclosure, the gradient amplifier 32 may be implemented according to the circuit diagram of FIG. 6. In addition, the gradient amplifier 32 may include a plurality of sub gradient amplifiers and in this case, each sub gradient amplifier may be implemented according to the circuit diagram of FIG. 6, but is not limited thereto.

Referring to FIG. 6, the gradient amplifier 32 may include at least one MOSFET. For example, the gradient amplifier 32 may include at least one N-channel MOSFET, but is not limited thereto.

According to the embodiment of the present disclosure, the gradient amplifier 32 may include an H-bridge circuit. In this case, the H-bridge circuit may be implemented with at least one MOSFET. In addition, the gradient amplifier 32 may include a boot strap circuit. In this case, the boot strap circuit may be implemented with at least one diode and at least one capacitor. In this case, the boot strap circuit may be used to maintain a high-voltage level.

According to the embodiment of the present disclosure, a magnetic resonance circuit system may include a gradient magnetic field generation module. The gradient magnetic field generation module means a module which generates the gradient magnetic field to form the gradient magnetic field. The gradient magnetic field generation module may include the gradient amplifier 32 and the gradient magnetic field coil 24.

The gradient amplifier 32 may apply the current to the gradient magnetic field coil 24 under the control of the gradient magnetic field control unit 54. In this case, the gradient amplifier 32 may supply the current to the gradient magnetic field coil 24 for a predetermined time and stop supplying the current when the predetermined time has elapsed.

According to the embodiment of the present disclosure, the gradient amplifier 32 applies various currents to the coil group under the control of the gradient magnetic field control unit 54 to generate gradient magnetic fields having various magnitudes and directions. For example, the gradient amplifier 32 applies the current to the coil group to control at least one of a shape of the gradient magnetic field, the strength of the gradient magnetic field, and a slew rate of the gradient magnetic field generated by the coil group.

The aforementioned description of the present disclosure is used for exemplification, and it can be understood by those skilled in the art that the present disclosure can be easily modified in other detailed forms without changing the technical spirit or requisite features of the present disclosure. Therefore, it should be appreciated that the aforementioned embodiments are illustrative in all aspects and are not restricted. For example, respective constituent elements described as single types can be distributed and implemented, and similarly, constituent elements described to be distributed can also be implemented in a coupled form.

The scope of the present disclosure is represented by claims to be described below rather than the detailed description, and it is to be interpreted that the meaning and scope of the claims and all the changes or modified forms derived from the equivalents thereof come within the scope of the present disclosure.

Related contents in the best mode for carrying out the present disclosure are described as above.

The present disclosure relates to a gradient magnetic field generation module and may be used in a magnetic resonance imaging system.

What is claimed is:

1. A system for generating gradient magnetic fields within a volume for use with magnetic resonance imaging, comprising:
    a main magnet configured to generate a static magnetic field along a longitudinal axis of the volume,
    a plurality of gradient magnetic field coils arranged around the volume to generate a gradient magnetic field along the longitudinal axis, the plurality of gradient magnetic field coils comprising a plurality of coil groups grouped into a plurality of pair coil groups, wherein each coil group in the plurality of pair coil groups is separated from a coil group in another of the plurality of pair coil groups by an interval along the longitudinal axis of the volume,
    a gradient magnetic field amplifier for independently applying current to each of the plurality of pair coil groups, and
    a gradient magnetic field control unit configured to control the gradient magnetic field amplifier so as to independently adjust a shape of the gradient magnetic field, a strength of the gradient magnetic field, and a slew rate of the gradient magnetic field generated by each of the pair coil groups.

2. The system of claim 1, wherein the gradient magnetic field control unit controls the magnetic field amplifier so as to adjust current applied to each of the pair coil groups such that a magnitude of current flowing to each of the plurality of pair coil groups is different.

3. The system of claim 1, wherein each of the pair coil groups comprises a first coil group and a second coil group, and wherein a direction of current which flows in the first coil group is opposite of a direction of current which flows in the second coil group.

4. The system of claim 1, wherein two coil groups of the plurality of gradient magnetic field coils that are adjacent to each other are arranged to form one of the plurality of pair coil groups.

5. The system of claim 1, wherein the gradient magnetic field that is formed along the longitudinal axis is a linear gradient magnetic field for acquiring an image of the object.

6. The system of claim 1, wherein the gradient magnetic field that is formed along the longitudinal axis is a non-linear gradient magnetic field for acquiring an image of the object.

7. The system of claim 1, wherein the gradient magnetic field amplifier comprises a plurality of sub gradient amplifiers.

8. The system of claim 1, wherein the gradient magnetic field control unit applies a pulsed control signal to the gradient field amplifier.

9. The system of claim 8, wherein the pulsed signal comprises an intensity, duration, and timing.

* * * * *